(12) United States Patent
Haniff et al.

(10) Patent No.: US 6,436,235 B1
(45) Date of Patent: Aug. 20, 2002

(54) N-SUBSTITUTED PERFLUOROALKYLATED PYRROLIDINES AND PROCESS FOR MAKING THEM

(75) Inventors: Marlon Haniff, West Orange, NJ (US); John Jennings, Bronx, NY (US); Karl Friedrich Mueller, New York, NY (US); Shobha Kantamneni, White Plains, NY (US)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 09/691,486

(22) Filed: Oct. 18, 2000

Related U.S. Application Data

(60) Provisional application No. 60/228,657, filed on Aug. 29, 2000, and provisional application No. 60/160,825, filed on Oct. 21, 1999.

(51) Int. Cl.[7] .................. D21H 19/14; D21H 27/22; C07D 207/04; C07D 207/06

(52) U.S. Cl. .................. 162/135; 162/158; 162/183; 548/400; 548/539; 548/524; 548/569

(58) Field of Search .................. 548/400, 524, 548/539, 569; 162/135, 158, 183

(56) References Cited

U.S. PATENT DOCUMENTS

| | | | |
|---|---|---|---|
| 3,535,381 A | 10/1970 | Hauptschein et al. | 260/570.9 |
| 3,763,225 A | 10/1973 | Foulletier et al. | 260/486 |
| 3,996,281 A | 12/1976 | Huber-Emden et al. | 260/561 |
| 5,427,859 A | 6/1995 | May | 428/421 |
| 5,580,992 A | 12/1996 | Tarumi et al. | 549/346 |

OTHER PUBLICATIONS

Brace, Neal, O. "Cyclization of N–Substituted Diallylamines to Pyrrolidine Derivatives During the Radical Addition of Perfluoroalkyl Iodides", (Journal of Organic Chemistry, 1971, 36(21) pp. 3187–3191).*
Chem. Abstr. 129:54119, Accession No. 1998:335551, for JP 10139747.
Chem. Abstr. 105:43535, Accession No. 1986:443535, for EP 177122.
Chem. Abstr. 116:174985, Accession No. 1992:174985, for JP03261749.
N. Brace, Journal of Polymer Science: Part A–1, vol. 8, pp. 2091–2102, (1970).
N. Brace, Journal of Organic Chemistry, vol. 36, pp. 3187–3191 (1971).

* cited by examiner

Primary Examiner—Robert W. Ramsuer
Assistant Examiner—Ebenezer Sackey
(74) Attorney, Agent, or Firm—Kevin T. Mansfield

(57) ABSTRACT

N-substituted perfluoroalkylated pyrrolidines of the formula III

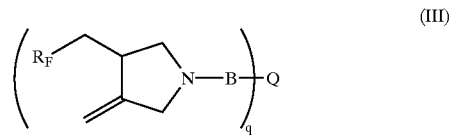

where $R_F$, B, Q and q are as defined herein are prepared from diallylamine, a perfluoroalkyl iodide and an amino-reactive compound selected from the group of carboxylic acids, anhydrides, acid chlorides, oxiranes, haloalkanes, isocyanates, ureas and (meth)acrylic compounds. These compounds are useful as specialty surfactants and as oil-proofing agents for paper and textiles. Polymers derived from the (meth)acrylamides are useful to impart water, oil and grease repellency to various substrates.

15 Claims, No Drawings

N-SUBSTITUTED PERFLUOROALKYLATED PYRROLIDINES AND PROCESS FOR MAKING THEM

This application claims the benefit under 35 U.S.C. 119(e) of U.S. Provisional Applications No. 60/160,825, Filed Oct. 21, 1999 and Ser. No. 60/228,657, Filed Aug. 29, 2000.

FIELD OF INVENTION

The present invention relates to N-substituted perfluoroalkylated pyrrolidines, reaction products thereof and the use of these reaction products as specialty surfactants, as oil- and grease-proofing agents for paper, textiles and hard surfaces such as masonry and wood.

BACKGROUND OF INVENTION

Perfluoroalkylated polymers which are used for treatment of textile and paper products to impart water, oil and grease repellency are almost exclusively derived from $R_F$-substituted acrylates or methacrylates, where $R_F$ represents a perfluorinated alkyl or alkenyl moiety. Certain $R_F$-acrylamide derivatives, although described in the literature, have not found a use in the market because of their uneconomical synthesis cost. A novel $R_F$-acrylamide has now been found which is easily prepared in high yield from readily available starting materials, i.e. diallylamine, an $R_F$-iodide and a difunctional acryloyl derivative, preferably 3-chloropropanoic acid chloride. Reaction products of this $R_F$-acrylamide have diverse uses.

U.S. Pat. No. 3,535,381 describes the synthesis of $R_F$-substituted amines and (meth)acryl-amides thereof by reaction of $R_F$-ethylene with a primary amine with elimination of hydrofluoric acid, followed by reaction with methacroyl chloride. The yield of $R_F$-amine based on the $R_F$-iodide is about 60%. U.S. Pat. No. 3,996,281 describes the synthesis of $R_F$-amines and derived (meth)acrylates from $R_F$-epoxides or $R_F$-chlorohydrins by reaction with primary or secondary amines. The necessity of preparing an $R_F$-epoxide first makes this approach very impractical. Other previously described $R_F$-acrylamides are described in JP 10139747 A2, for example $R_F$-ethylacrylamide synthesized from acryloyl chloride and 1,1-dihydroheptafluorobutylamine. EP-A 177122 describes an $R_F$-substituted urethane derived from acryloyl isocyanate.

U.S. Pat. No. 3,996,281 describes N,N-di-$R_F$-acrylamides derived from an $R_F$-epoxide, an amine and acryloyl chloride. U.S. Pat. No. 3,763,225 describes an $R_F$-acrylamide derived by reaction of $R_F$-iodide with a primary amine and amidification with acyloyl chloride in pyridine. JP 03261749 describes an N-$R_F$-ethyl-N-allyl diacrylamide prepared from $R_F$-ethyl iodide by reaction with allylamine and acryloyl chloride.

The free radical-induced addition of perfluoroalkyl iodides to N,N-diallyl derivatives and subsequent formation of pyrrolidines by ring closure is well documented. Brace, in J. Polymer Science, Part A-1, 8, 2091 (1970) describes the synthesis of 3-(perfluoroalkyl)methyl-4-methylenepyrrolidine of the formula I

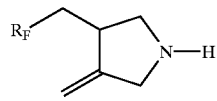

(I)

by addition of $R_F$-iodide to diallylcyanamide and subsequent hydrolysis; large amounts of the corresponding pyrrolidine amide are formed as a by-product. In the case of diallylamine itself, Brace (J. Org. Chem. 36, 3187 (1971)) found that the intermediate $R_F$-iodide adduct formed a polymeric $R_F$-amino compound by substitution; the desired $R_F$-pyrrolidine amine of the formula I was not obtained.

The N-benzoyl, N-acetyl and N-trifluoroacetyl, N-carbonitrile, N-propionitrile and N-carboxamide derivatives of 3-(perfluoroalkylmethyl)4-methylenepyrrolidine are known from Brace, J. Org. Chem. 36, 3187 (1971), and maleic acid amide copolymers are known from U.S. Pat. No. 5,427,859. Each of these products however is made by reacting the N-substituted diallylamine with $R_F$-iodide, and it is often almost impossible to remove the eliminated iodide salts from the final product, especially if the product is water soluble.

It is an object of the present invention to provide a convenient high yield synthesis of 3-(perfluoroalkyl) methyl4-methylenepyrrolidine. It is a further object of the present invention to provide fluorinated derivatives thereof, such as amides, ureas, ethers and urethanes, by reaction of 3-(perfluoroalkyl)methylmethylenepyrrolidine with amino-reactive compounds such as carboxylic acids, acid chlorides, anhydrides, oxiranes, isocyanates, halo-alkanes, ureas and (meth)acrylates or other vinyl compounds, which fluorinated derivatives are substantially free of iodide salts and which are useful as specialty surfactants and as oil proofing agents for paper and textiles.

It is a further object of the present invention to provide a novel monomer, 1-(meth)acryloyl-3-(perfluoroalkyl) methyl4-methylenepyrrolidine of the formula II

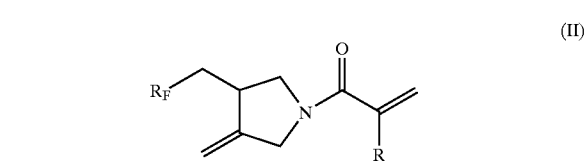

(II)

wherein R is hydrogen or methyl and $R_F$ is a perfluorinated alkyl or alkenyl moiety and a method for its synthesis from diallylamine, $R_F$-iodide and a (meth)acryloyl derivative using a novel process for the addition of the $R_F$-iodide to the allylic double bond.

It is a further object of the present invention to provide polymers derived from 1-(meth)acryloyl-3-(perfluoroalkyl) methyl-4-methylenepyrrolidine which are useful to impart water, oil and grease repellency to substrates such as wood, paper, textiles, metal, glass or masonry.

The inventive $R_F$-(meth)acrylamides can readily be copolymerized with other vinyl monomers, such as (meth)acrylates, (meth)acrylamides, styrene or vinyl ethers or -esters. The hydrolytic stability of polymers based on tertiary acrylamides gives them a special advantage over the more commonly used (meth)acrylates, because it allows the synthesis of anionic water-dispersible polymers which need to be stable at alkaline pH.

DETAILED DISCLOSURE

The present invention relates to novel $R_F$-pyrrolidines of the formula III

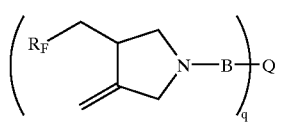

(III)

in which
- $R_F$ is a monovalent perfluorinated alkyl or alkenyl, linear or branched organic radical having four to twenty fully fluorinated carbon atoms,
- B is a direct bond, —C(=O)— or —C(=O)—N—,
- q is an integer from 1 to 10 in which,
- when q is 1,
  - Q is a monovalent organic radical with 2 to 200 carbon atoms and which can contain one or more unsaturated groups and is optionally interrupted by one or more —O— or —S— linkages or tert. amino groups, and which is unsubstituted or substituted by one or more hydroxyl, tert. amino, amide, $R_F$, —P(=O)(OH)$_2$, —SO$_3$H or —COOH groups, or is also NH$_2$ if B is —C(=O)—, and, when q is greater than 1,
  - Q is a di- or polyvalent organic radical with 2 to 200 carbon atoms which can be interrupted by one or more —O— or —S— linkages, amide or tert. amino groups, and which is unsubstituted or substituted by one or more hydroxyl, tert. amino, amide or carboxyl groups; —C(=O)— or a di- or triradical derived from cyanuric chloride,
  - with the proviso that if Q is —C(=O)—, B is a direct bond, and wherein any amino groups are optionally partially or fully salinized, quaternized or in the form of the corresponding N-oxides.

Preferably $R_F$ is saturated and contains 4–12 carbon atoms, is fully fluorinated and contains at least one terminal perfluoromethyl group; most preferably $R_F$ is saturated and contains 6–10 fully fluorinated carbon atoms.

Preferably q is 1 or 2.

Preferred are compounds of the formula III wherein q is 1 and B-Q is —(CH$_2$)$_{1-3}$COOH; —CH$_2$—C(=O)NH$_2$; —C(=O)—CR=CH$_2$; —C(=O)—COOH; —C(=O)—(CH$_2$)$_{2-3}$—COOH; —C(=O)—CH=CH—COOH; —C(=O)—C(=CH$_2$)—CH$_2$—COOH and —C(=O)—CH$_2$—C(=CH$_2$)—COOH; —C(=O)—(C$_6$H$_4$)—COOH; —C(=O)—(C$_6$H$_8$)—COOH; —C(=O)—(C$_6$H$_5$R$_F$)—COOH; —C(=O)—(C$_7$H$_6$)—COOH; —C(=O)—(C$_8$H$_8$)—COOH; —C(=O)(CH$_2$)$_8$CH=CH$_2$; —CH$_2$—CHOH—CH$_2$—O—CH$_2$—CH=CH$_2$; —C(=O)CH$_3$; —CH$_2$CH$_2$N(CH$_3$)$_2$; —C—CH$_2$CH$_2$CH$_2$N(CH$_3$)$_2$; —CH$_2$—CH(OH)—CH$_2$—N(CH$_3$)$_3$$^+$; —CH$_2$—CHOH—CH$_2$—O—(CH$_2$CHR—O)$_m$R$_1$; —P(=O)(OH)$_2$ or —SO$_3$H, in which R is hydrogen or methyl, m is a number from 1 to 20 and R$_1$ is hydrogen, an alkyl group with 1 to 20 carbon atoms, or a phenyl group substituted by p-octyl- or p-nonyl, or SO$_3$H.

R and R$_1$ are preferably hydrogen. Preferably m is a number from 1 to 10.

Most preferred are compounds of the formula III wherein q is 1 and B-Q is —C(=O)—CR=CH$_2$; —CH$_2$—COOH; —C(=O)—(CH$_2$)$_2$—COOH; —C(=O)—(C$_6$H$_4$)—COOH; —C(=O)—(C$_6$H$_5$R$_F$)—COOH or —C(=O)—(C$_6$H$_8$)—COOH wherein R is hydrogen or methyl. Especially preferred are 1-(meth)acryloyl-3(perfluoroalkyl)methyl4-methylene compounds of the formula II

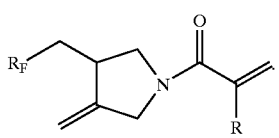

(II)

Also preferred are compounds of the formula III wherein q is 2, B is a direct bond and Q is —CH$_2$—CHOH—CH$_2$—O—(CH$_2$ CHR—O)$_m$—((CH$_2$—CHR$_2$—O)$_n$—(CH$_2$—CHR$_3$—O)$_l$)$_z$—CH$_2$—CHOH—CH$_2$—; —CH$_2$CH$_2$—; or —CH$_2$—CHOH—CH$_2$—; wherein R, R$_2$ and R$_3$ are independently of each other hydrogen or methyl, m, n and l are a number from 1 to 20 and z is zero or 1; with the proviso that if R$_2$ is hydrogen, R and R$_3$ are methyl and vice versa; or —CH$_2$ CH$_2$—C(=O)—NH—CH$_2$—NH—C(=O)—CH$_2$CH$_2$—; or where B is —C(=O)—NH— and Q is the diradical hydrocarbon residue of p- or m-toluene diisocyanate, isophorone diisocyanate, 3,3,4(3,4,4) trimethylhexane-1,6diisocyanate or hexane-1, 6diisocyanate; or where B is —C(=O)— and Q is —(C$_6$H$_2$)(—COOH)$_2$)—, —(C$_{13}$H$_6$O)(—COOH)$_2$)—, or is C$_{2-C10}$alkenylene or —C$_6$-C$_{10}$arylene.

Most preferred are compounds of the formula III where q is 2 and B-Q is —CH$_2$—CHOH—CH$_2$; —C(=O)—CH$_2$CH$_2$—C(=O)— or —C(=O)—(—C$_6$H$_2$(—COOH)$_2$)—C(=O)—.

Compounds which are 3-(perfluoroalkyl)methyl-4-methylenepyrrolidines of the formula I

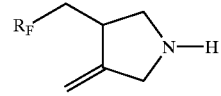

(I)

are useful as intermediates to prepare compounds of the formula III. The synthesis of a compound of the formula I is preferably carried out stepwise by reaction of diallylamine with an equivalent amount of $R_F$-iodide in an aqueous medium at temperatures of from 5 to 50° C., using sodium dithionite as initiator, followed by elimination of HI with a base, to form a 3-(perfluoroalkyl)methyl-4-methylenepyrrolidine of the formula I.

By adjusting the reaction mixture to an alkaline pH, this intermediate can be washed substantially free of iodide salts. This leads to an iodide-free end product in the subsequent step.

To prepare a compound of the formula III, the 3-(perfluoroalkyl)methyl-4-methylenepyrrolidine intermediate of the formula I is reacted with an anhydride such as oxalic-, glutaric-, alkenyl-succinic-, succinic-, tetrahydrophthalic-, norbornene-; methendic-, maleic-, trimellitic or itaconic anhydride, to form the corresponding amic-acid;

with a dianhydride such as pyromellitic anhydride or benzophenone-tetracarboxylic acid dianhydride to form the corresponding di-amic acid;

with an acyl halide such as benzoyl chloride or acetyl chloride or with a diacyl halide such as oxalylchloride, or an alkyl ester such as ethyl undecylenate or a dialkyl ester such as dimethyl succinate, to form the corresponding amides or diamides;

with a halogenated organic compound such as 1,4-dichloromethylbenzene, chloroacetic acid, chloropropionic acid or chloroacetamide to form the corresponding tertiary amine or tertiary amine-acid;

with a diisocyanate such as isophorone diisocyanate, toluene diisocyanate, 1,6-diisocyanatohexane or 1,6-diisocyanato-3,3,4(3,4,4)-trimethylhexane to form the corresponding diurethane;

with an oxirane or a polyoxirane compound such as epichlorohydrin, ethylene oxide, propylene oxide, cyclohexane oxide, styrene oxide, allyl glycidyl ether, and the diglycidyl ether of bisphenol A, bisphenol F or 1,4-butanediol, to form the corresponding hydroxy-tertiary amino compounds;

or with a phosphoric acid derivative such as $POCl_3$, polyphosphoric acid or sodium metaphosphate to form the corresponding phosphamic acids.

The compounds of formula III can also be made by first preparing N,N-diallyl intermediates either through the reaction of diallylamine with the reactants mentioned above, or by reaction of primary amines Q—$(NH_2)_q$ with two equivalents of allyl chloride, in either case adding the $R_F$-iodide during the last step. A large variety of primary amines and polyamines can be used to make compounds of formula III in which B is a direct bond and Q is a hydrocarbon residue as defined above. Typical amines are aliphatic, cycloaliphatic and aromatic amines and substituted amines with 1 to 20 carbon atoms such as stearylamine; glycine, lysine and other amino acids; N,N-dimethylpropane-1,3-diamine, p-amino benzoic acid, sulfanilic acid, N,N'-bis-3-aminopropyl piperazine, ethylendiamine, diethylenetriamine and bis-(3-aminopropyl)ethylenediamine.

The radical Q can itself be $R_F$-substituted if it is derived for example from $R_F$-undecylenic acid, 3-$R_F$-tetrahydrophthalic anhydride or 3-$R_F$-4-iodo-norbornene anhydride. In such cases it is preferable to first react diallylamine with any of the unsaturated precursors - undecylenic acid, tetrahydrophthalic anhydride and/or norbornene anhydride—then to add the $R_F$-iodide last and simultaneously to both types of double bonds in the corresponding diallyl amides. Such compounds of formula (III) in which Q is substituted by an $R_F$-group are another object of this invention.

Compounds of formula III containing tertiary amino groups can, if desired be quatemized with quatemizing agents such as alkyl halides, chloroacetic and chloropropionic acids, benzyl chloride, allyl chloride, chloroacetamide, propiolactone or propanesultone. They can also be oxidized to the corresponding N-oxides with a peroxy compound such as $H_2O_2$ or salinized with an inorganic or preferably organic acid. Such compounds are another object of this invention.

The synthesis of the preferred 1-(meth)acryloyl-3-(perfluoroalkyl)methyl-4-methylene compounds of the formula II (II)

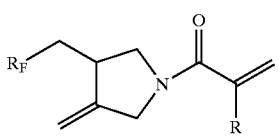

wherein R is hydrogen or methyl and $R_F$ is as previously defined can be carried out in various ways. One method entails the addition of $R_F$-iodide to diallylamine, forming a 3-(perfluoroalkyl) methyl-4-methylenepyrrolidine of the formula I, followed by reaction with (meth)acryloyl chloride, (meth)acrylic acid or a (meth)acrylic acid ester and finally elimination of Hl with a base. Invariably a large amount of by-product is formed as a result of Michael addition of the pyrrolidine to the acrylic double bond. In the case of the acrylamide, this problem can be circumvented by using 3-chloropropionyl chloride (CPC) to form the amide, followed by elimination of HCl with a base to form the corresponding acrylamide.

An alternative and preferred method of preparing a 1-acryloyl-3-(perfluoroalkyl)methyl-4-methylenepyrrolidine of the formula IIa (IIa)

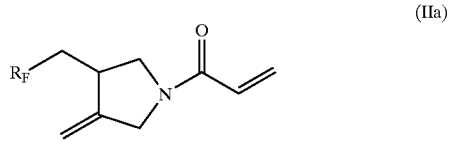

comprises first reacting 3-chloropropionyl chloride (CPC) with diallylamine to form N,N-diallyl-3-chloropropaneamide, then reacting this product with $R_F$-iodide followed by eliminating HCl and Hl by dehydrohalogenating with a base such as an alkali metal hydroxide. The product of the formula IIa is then washed with water followed by separating the aqueous layer.

The addition of $R_F$-iodide to the diallylamine moiety is accomplished in an aqueous medium advantageously containing from 5 to 50% by weight of a water-soluble cosolvent such as an alcohol or ketone, to compatibilize both reactant phases. Preferred cosolvents are lower alcohols such as methanol, ethanol, n- and iso-propanol and t-butyl alcohol. A suitable free radical initiator for the addition of $R_F$-iodide is 0.01 to 10 mole %, preferably 0.1 to 5 mole %, based on the $R_F$-iodide of an alkali metal dithionite, preferably sodium or potassium dithionite, preferably in the presence of a water-soluble aldehyde such as formaldehyde or glyoxal or, especially, in the presence of an aldehyde adduct such as hydroxymethane sulfinic acid, sodium salt (the addition product of formaldehyde and sodium dithionite). It is commercially available as the dihydrate from Aldrich Chemical Company. It is also commercially available under the tradename Rongalite. The aldehyde or aldehyde adduct is believed to scavenge bisulfite ions, which would otherwise react with the primary chloride or with the acrylic double bond of 3-chloropropionyl chloride to form surfactant-like molecules by forming an adduct with them.

Suitably the reaction is conducted at temperatures of 0 to 60° C.

The addition of $R_F$-iodide to double bonds only in the presence of equivalent amounts of dithionite or Rongalite is known from Huang, Acta Chimica Sinica, 44 488, (1986) and Huang, Chin. J. Chem. (1990), 191, respectively.

U.S. Pat. No. 5,585,517 describes the addition of $R_F$-iodide to allyl alcohol using an azo-type free radical initiator together with an alkali metal bisulfite or dithionite ion, which in this case only serves to reduce any free iodine which would otherwise inhibit the reaction. Copending U.S. patent application Ser. No. 09/234,251 describes the addition of $R_F$-iodide to allylic double bonds at low temperature, using only catalytic amounts of an alkali metal dithionite to create ion-radicals for initiation, with no mention of the presence of an aldehyde. In the present situation, where the end product is an acrylate, the reaction is complicated by the fact that bisulfite ion (the decomposition product of the dithionite) not only easily displaces a primary chloride, but can also add to the acrylic double bond which is formed under the basic conditions required for HCl elimination, in either case forming a very potent $R_F$-sulfonate surfactant as by-product. This reduces the yield of the desired acrylamide product and makes isolation by phase separation very difficult due to excessive foaming and emulsification. This problem is circumvented by the use of an aldehyde or aldehyde adduct to stabilize the alkali metal dithionite. Most preferred is the use of Rongalite, the above-mentioned complex of formaldehyde and sodium dithionite.

An added advantage of Rongalite is that it is more stable than an alkali metal dithionite alone at the low pH required to carry out the $R_F$-iodide addition reaction; at a high pH HCl is eliminated prematurely.

Thus another object of this invention is a process for the addition of $R_F$-iodide to an olefin which comprises reacting an $R_F$-iodide with an olefin in the presence of 0.01 to 10 mole %, preferably 0.1 to 5 mole %, based on the $R_F$-iodide of a combination an alkali metal dithionite and a water-soluble aldehyde or an adduct of an alkali metal dithionite and a water-soluble aldehyde, where $R_F$ is as defined above. Preferably the alkali metal dithionite is sodium or potassium dithionite and the water-soluble aldehyde is formaldehyde or glyoxal. The preferred adduct of an alkali metal dithionite and a water-soluble aldehyde is hydroxymethane sulfinic acid, sodium salt, the addition product of formaldehyde and sodium dithionite. Advantageously the reaction is carried out in an aqueous medium containing 5–50% by weight of a water-soluble cosolvent and at temperatures of 0 to 60° C.

Preferred bases for the subsequent dehydrohalogenation are alkali metal hydroxides, in particular sodium and potassium hydroxide.

To avoid polymerization during the dehydrohalogenation, it is advisable to carry out the reaction in the presence of a polymerization inhibitor such as phenothiazine, p-methoxyphenol or other conventional inhibitors known in the art.

When the compounds of the present invention are used as grease and oil repellent paper sizing agents, they are applied by methods known per se in amounts which are sufficient to deposit from 0.005 to 0.5% of organically bound fluorine by weight based on the dry paper weight. The compounds of the present invention can be applied either externally in topical applications, for instance in a size press to the surface of paper or cardboard. They can also be applied internally, by adding them to an aqueous pulp together with other wet-end chemicals, as described for instance in U.S. Pat. No. 5,091,550, the disclosure of which is incorporated by reference, and more generally in W. F. Reynolds, "The Sizing of Paper", TAPPI Press, 1989.

It has been very unexpectedly found that the reaction products of 3(perfluoroalkyl)methyl-4-methylenepyrrolidine with anhydrides and dianhydrides perform as well as the best available polymeric fluorinated compounds as treatments for the grease-repellent paper that is employed in pet-food packaging; no other small fluorinated molecule has given equivalent performance.

The following examples illustrate various embodiments of how to make and use the invention, and are not to be interpreted as limiting the scope of the appended claims. In the examples, all parts are by weight unless otherwise specified. A perfluoroalkyl iodide mixture of the formula $C_nF_{2n+1}-I$ with n=4 to 14 was obtained from DuPont under the product name ZONYL® TELA-N. It has the following average telomer distribution: $C_6$=6% maximum, $C_8$=50±3%, $C_{10}$=29±2%, $C_{12}$=11±1%, $C_{14}$ and higher=4% maximum, respectively. $C_6F_{13}I$ was obtained from Clariant Chemical Corporation.

EXAMPLE 1

Synthesis of N-Acryloyl-3-(perfluoroalkyl)methyl-4-methylene Pyrrolidine

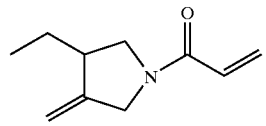

a) 3-Chloropropionyl chloride (CPC) (100 g, 0.783 mole, 98% pure) and aqueous 31.8% sodium hydroxide (99.3 g, 0.791 mole), are added while stirring to diallylamine (76.1 g, 0.783 mole) over one hour at 0–5° C. with the pH controlled at 8–8.5 using a pH-meter. After the addition, the two phase mixture is allowed to warm up to 23° C. and extracted twice with diisopropyl ether (40 ml). The solvent is evaporated under vacuum to give a clear, colorless liquid in quantitative yield. The structure of N,N-diallyl-3-chloropropionamide is confirmed by analysis: Spectral data: $^1$H NMR (500 MHz, CDCl$_3$); δ=5.14, 5.21 (m, 4H, CH$_2$=CH), 5.75 (m, 2H, CH$_2$=CH), 3.99 (d, 2H, N—CH$_2$), 3.65 (d, 2H, N—CH$_2$), 2.78 (t,2H, $^3$J=6.70 Hz, CH$_2$C=O), 3.81 (t, 2H, $^3$J=6.70 Hz, Cl—CH$_2$). Elemental Analysis: calc. for C$_9$H$_{14}$ClNO: C, 57.54; H, 7.46; N, 7.46; Cl, 18.91. Found: C, 57.41; H, 7.79; N, 7.16; Cl, 18.62.

b) Sodium dithionite (0.35 g, 1.78 mmol, 88%) is added to a mixture of the reaction product of Example 1a) (5.2 g, 27.7 mmol), perfluoroalkyl iodide (R$_F$I, DuPont's Zonyl TelA-N) with a homologue distribution of 53.0% C$_8$F$_{17}$I, 30.6% C$_{10}$F$_{21}$I, 11.7% C$_{12}$F$_{25}$I, 3.6% C$_{14}$F$_{29}$I, and 1.0% C$_{16}$F$_{33}$I (16.6 g, 27.2 mmol), 9.1 g water, and 8.7 g tert.-butyl alcohol (t-BuOH) at 19° C. with stirring. The reaction temperature spontaneously increases to 49° C. and is allowed to cool back to room temperature. After a total of two hours, the reaction is over (<0.5 wt. % R$_F$I remaining by GC). Phenothiazine (5 mg) and potassium hydroxide (9.2 g, 81.9 mmol, 50%) are added to the mixture and it is stirred at 60–64° C. for 6 hours to carry out the dehydrohalogenation. Excess base is neutralized with dilute sulfuric acid and t-BuOH/H$_2$O is azeotroped off under reduced pressure. The mixture is washed twice with 40 ml 2-pentanone at 65° C. Substantial foaming is observed during the washing and distillation. Since bisulfite is a decomposition product of dithionite, the foaming is believed to be due to a sulfonate surfactant that is formed from bisulfite addition to the acrylic double bond. The solvent is carefully evaporated under vacuum at 40° C. to give a yellow solid (13.9 g, 80%, m.p. 55–63° C.). (A lower than expected yield is obtained with most of the losses occurring during phase separation due to the presence of the sulfonate by-product).

A portion of the product is purified further by applying a band of material dissolved in ether to a preparative TLC plate (Silica gel GF, 1000 microns, 20×20 cm, with preadsorbent zone, UV$_{254}$, ether mobile phase) and scraping off the band at R$_f$=0.31. This material is washed with methanol, filtered and dried under vacuum. The solid residue is analyzed and its N-acryloyl-3-(perfluoroalkyl)methyl4-methylene pyrrolidine structure confirmed by $^1$H NMR (500 MHz, CDCl$_3$); δ=6.41 (m, 2H, CH$_2$=CH), 5.74 (m,1H, CH$_2$=CH), 5.20, 5.06 (d, 2H, CH$_2$=C), 4.25 (d, 2H, N—CH$_2$C), 3.32, 4.12 (m, 2H, AB portion of ABX, N—CH$_2$CH), 3.10, 3.21 (bm, 1H, CH$_2$CHCH$_2$), 2.13, 2.52 (bm, 2H, CF$_2$CH$_2$). Elemental Analysis: calc. for C$_{18.27}$H$_{12}$F$_{19.54}$NO: C, 34.66; H, 1.90; F, 58.70; N, 2.21%. Found: C, 34.44; H, 1.63; F, 56.95; N, 2.21%.

EXAMPLE 2

Improved synthesis of N-Acryloyl-3-(perfluoroalkyl)methyl-4-methylene Pyrrolidine to Reduce by-Product Formation and Increase Isolated Yield An aqueous solution of Rongalite (trade name for the addition product of formaldehyde and sodium dithionite), (0.52 g, 3.4 mmol, 30%) is added to a mixture of the reaction product of Example 1a) (30.8 g, 0.17 mol), perfluoroalkyl iodide ($R_F$I, DuPont's Zonyl TelA-N) with a homologue distribution of 53.0% $C_8F_{17}$I, 30.6% $C_{10}F_{21}$I, 11.7% $C_{12}F_{25}$I, 3.6% $C_{14}F_{29}$I, and 1.0% $C_{16}F_{33}$I (100.3 g, 0.169 mol), 57.3 g water, and 51.9 g tert.-butyl alcohol (t-BuOH) at 75° C. with stirring. The reaction mixture begins to spontaneously reflux at 82° C. and is allowed to cool back to 73–75° C. where it is maintained for two hours, after which time <1 wt. % $R_F$I remains as determined by GC. Phenothiazine (58 mg) followed by 45% potassium hydroxide (53 g, 0.425 mol), is added to the mixture, which is then stirred at 73–77° C. for 4 hours to carry out the dehydrohalogenation. The t-BuOH/$H_2O$ is azeotroped off under reduced pressure with no foaming evident and the mixture is washed twice with 50 ml 2-pentanone at 65° C. The solvent is evaporated under high vacuum at 60° C. to give 100.1 g of a yellow solid, corresponding to 99% yield. Chemical shifts and TLC $R_f$ values match those of the desired compound. By proton NMR and chromatography, a cleaner product is obtained using Rongalite as the initiator as opposed to dithionite.

EXAMPLE 3

Comparative Example Using a Conventional Free-radical Initiator and Process

The process of Example 2 is repeated, but using 2,2'-azobis(2-methylbutyronitrile) (VAZO-67) in place of Rongalite as initiator. After 5 hours at 78° C., 95 mole % of the starting $R_F$I remains unreacted as determined by GC.

EXAMPLE 4

Synthesis of $R_F$-Acrylamide Copolymer

A flask fitted with a reflux condenser is charged with 3.0 g of N-acryloyl-3-(perfluoroalkyl)-methyl4-methylene pyrrolidine synthesized according to Example 2, 0.5 g of N,N-diethyl-aminoethyl methacrylate, 0.3 g of methyl methacrylate and 5.0 g of methyl isobutyl ketone. The reaction flask is purged with nitrogen at 40° C. and 0.05 g of azobisisobutyronitrile are added. The temperature of the stirred mixture is then raised to between 60 and 65° C. and held there for 20 hours. Then another 0.03 g of azobisisobutyronitrile are added and the mixture is stirred at 65° C. for another 16 hours. Finally, methyl methacrylate (0.05 g) and another charge of azobisisobutyronitrile (0.01 g) are added and the reaction is completed during further stirring at 65° C. for 4 hours. To the resulting viscous solution a mixture of water (20.0 g) and acetic acid (0.3 g) is added and the mixture is stirred for 15 minutes. The ensuing polymer solution is transferred into a round-bottom flask and methyl isobutyl ketone is removed under vacuum. The final aqueous solution is adjusted with water to give 20.0 g of a copolymer solution with 19% by weight solids content.

EXAMPLE 5

Synthesis of 3-(perfluoroalkyl)methyl-4-methylene Pyrrolidine

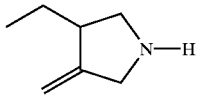

An aqueous solution of sodium dithionite (0.6 g, 2.87 mmol, 25%) is added to a mixture of diallylamine (5.6 g, 57.4 mmol), perfluoroalkyl iodide ($R_F$I; DuPont's Zonyl TelA-N) with a homologue distribution of 53.0% $C_8F_{17}$I, 30.6% $C_{10}F_{21}$I, 11.7% $C_{12}F_{25}$I, 3.6% $C_{14}F_{29}$I, and 1.0% $C_{16}F_{33}$I (35.0 g, 57.4 mmol), 18.0 g water, and 9.2 g methyl tert.-butyl ether at 13° C. with stirring. The reaction mixture spontaneously begins to exotherm, reaching a maximum temperature of 42° C. after about 15 minutes. It is allowed to cool back to room temperature over 45 minutes where it is maintained for 90 minutes, after which time <2 wt. % $R_F$I remains as determined by GC. A charge of 50% potassium hydroxide (9.0 g, 80.4 mmol), is added to the mixture, which is then stirred at 60–62° C. for 5 hours to carry out the dehydrohalogenation (reaction monitored by GC and $AgNO_3$ titration for iodide). The resulting product mixture is extracted thrice with 75 ml methyl tert.-butyl ether at 50° C., and the solvent is evaporated under high vacuum at 50° C. to give 30.7 g (93.7%) of white solid. The pyrrolidine structure is confirmed by $^1H$ NMR (500 MHz, $CD_3OD$): δ=4.9, 5.1 (d, d, 2H, $^2J$=2.3 Hz, $CH_2$=C), 3.4, 3.6 (dd, 2H, $^2J$=13 Hz, —NH—$CH_2$C), 3.3, 2.6 (m, 2H, $^2J$=15 Hz, $^3J$=8.5 Hz, —NH—$CH_2$CH), 2.9 (m, 1H, —$CH_2CHCH_2$), 2.2, 2.5 (m, 2H, $CF_2CH_2$). $^{13}C$ NMR (500 MHz, $CD_3OD$) d: 152.3, $CH_2$=C, 104.9, $CH_2$=C, 54.2, —NH—$CH_2$C, 51.8, —NH—$CH_2$CH, 37.3, —$CH_2CHCH_2$, 34.1 Hz, $CF_2CH_2$ (t, $^2J_{C-F}$=22.6 Hz).

EXAMPLE 6

N-Succinyl-3-(perfluoroalkyl)methyl-4-methylene Pyrrolidine

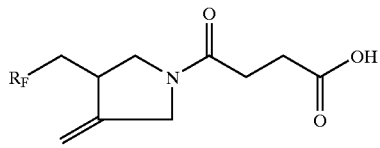

a) Preparation of N,N-Diallyl Succinamic Acid.

Powdered succinic anhydride (32.6 g, 32.6 mmol) is added over 30 minutes to diallylamine (30. g, 30.8 mmol) while the temperature is maintained at 20–25° C. with stirring. After the addition, the temperature is raised to 47° C. and held there for 2.5 hours, after which 1.4% diallylamine is unreacted by GC. The clear, amber liquid is analyzed by $^1H$ NMR (500 MHz, $CD_3OD$); δ=5.39, 5.23 (m, 2H, $CH_2$=CH), 5.20, 5.15 (dd, 4H, $CH_2$=CH), 3.90 (d, d, 4H, —N—$CH_2$), 2.65 (t, 2H, —$CH_2COOH$), 2.55 (t, 2H, —$CH_2CON$—). IR (film, NaCl), $_{n=CH}$ 993, 927 (olefin), $_{n=CN}$ 1415, $_{n=CO}$ 1474 acid), $_{n=C=O}$ 1624 (amide), $_{n=C=O}$ 1728 (acid), $_{n=CH}$ 3083, 2990 (aliphatic), $_{n=OH}$ 3300–2500.

b) $R_F$-iodide Addition.

To a solution of the reaction product of Example 6a (10.0 g, 49.0 mmol), 23.0 g water, and 12.0 g tert.-butyl alcohol (t-BuOH) is added sodium hydroxide (4.6 g, 57.5 mmol, 50%) to adjust the pH from 3.55 to 11.92. Then perfluoroalkyl iodide ($R_F$l, DuPont's Zonyl TelA-N) with a homologue distribution of 53.0% $C_8F_{17}$l, 30.6% $C_{10}F_{21}$l, 11.7% $C_{12}F_{25}$l, 3.6% $C_{14}F_{29}$l, and 1.0% $C_{16}F_{33}$l (28.3 g, 47.5 mmol) is added followed by sodium dithionite (0.4 g, 1.96 mmol, 88%). The reaction mixture temperature spontaneously increases from 22° C. to 54° C. After cooling and stirring for 90 minutes at 25–30° C., less than 1 wt. % $R_F$l is unreacted as determined by GC. Sodium hydroxide (4.7 g, 58.7 mmol) is added and the mixture is stirred at 45° C. for 4.5 hours to carry out the dehydroiodination step. The product mixture is then poured into 1 liter of acidified ice water, filtered, and dried to give a white powder in quantitative yield. Proton NMR confirms the suggested structure.

EXAMPLE 7

Synthesis and Performance of N-Succinyl-3 (perfluorohexyl)methyl-4-methylene Pyrrolidine as a Surfactant The procedure of Example 6 is repeated, but using in step b) as the $R_F$-iodide an equivalent amount of $C_6F_{13}$l. The resulting product is an anionic surfactant with the following properties in aqueous solution, as determined by surface tension measurements. The table shows the results in comparison with FORAFAC 1157, a benchmark surfactant from ATOCHEM Chem. Company.

| Compound | Surface Properties* of Aqueous Solutions with 0.041% F | | |
|---|---|---|---|
| | S.T. dynes/cm | I.T. | S.C. |
| Example 7 | 17.9 | 4.2 | 3.6 |
| FORAFAC 1157 | 16.6 | 6.1 | 3.0 |

*S.T. = surface tension; I.T. interfacial tension versus cyclohexane; and S.C. = spreading coefficient

EXAMPLE 8

Synthesis of 6-(3-Methylene4-perfluoroalkyl-pyrrolidine-1-carbonyl)-4-perfluoroalkyl-cyclohex-3-enecarboxylic Acid

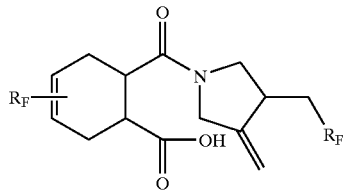

a) Preparation of N,N-Diallyl Tetrahydrophthalic Acid.

Flaked tetrahydrophthalic anhydride (24.6 g, 0.162 mol) is added portionwise to diallylamine (15.0 g, 0.154 mol) resulting in an exotherm from room temperature to 90° C. The mixture is then heated to 134° C. with stirring for 3 hours to give 39.2 g (98.9%) of a viscous, clear, and amber liquid that contains less than 5 mole % diallylamine by GC. Thin layer chromatography and GC show exclusively one component. $^1$H NMR (500 MHz, CDCl$_3$); δ=5.81, 5.71 (m, 2H, $H_3$ and $H_4$), 5.70 (m, 2H, $H_8$), 5.22, 5.13 (m, 4H, $H_9$ and $H_{10}$), 4.10–3.92 (m, 4H, $H_7$), 3.08(m, 1H, $H_6$), 2.96 (m, 1H, $H_1$), 2.52, 2.22 (m, 4H, $H_2$ and $H_5$).

b) $R_F$-iodide Addition

To a solution of the reaction product of example 7a (5.0 g, 19.4 mmol), 10.0 g water, and 6.0 g tert.-butyl alcohol (t-BuOH) is added sodium hydroxide (1.57 g, 19.6 mmol, 50%) to adjust the pH from 4.2 to 11.2. The solution is then heated to 60° C. and perfluoroalkyl iodide ($R_F$l DuPont's Zonyl Tela-N) with a homologue distribution of 53.0% $C_8F_{17l}$, 30.6%$C_{10}F_{21}$l,11.7% $C_{12}F_{25}$l, 3.6% $C_{14}F_{29}$l , and 1.0% $C_{16}F_{33}$l (23.4 g, 38.8 mmol) is added followed by a charge of Rongalite (0.19 g, 1.20 mmol) . The reaction mixture's temperature spontaneously increases to reflux and is maintained with stirring at 78° C. for 4 hours, resulting in a 96 wt. % $R_F$l conversion by GC. Sodium hydroxide (4.7 g, 58.7 mmol, 50%) is added and the mixture is stirred at 63° C. for 4.5 hours to carry out the deiodination step. The product mixture is then poured into acidified ice water, filtered, and dried to give an off-white powder (22.2 g, 94.9%). Proton NMR shows the downfield shifting of the olefinic hydrogen vicinal to the perfluoro group on the cyclohexenyl fragment and the overall spectrum is in agreement with the desired structure.

EXAMPLE 9

Synthesis of 4,6-bis-(3-Methylene-4-perfluoroalkyl-pyrrolidine-1-carbonyl)-isophthalic Acid

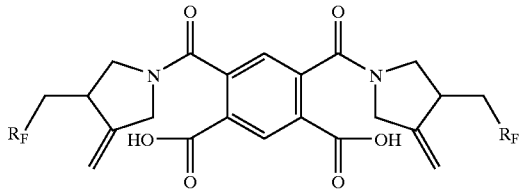

The pyrrolidine from Example 5 (13.0 9. 22.4 mmol) is stirred at 130° C. for 6 hours with pyromellitic anhydride (2.5 g, 11.1 mmol) and N-methylpyrrolidinone (4.4 g). GC analysis shows 94% of the pyrrolidine is converted to desired amide. An aqueous dispersion is then formulated with the following materials: 19.9 g of above product mixture, 41 g water, 4.0 g 20% ammonium hydroxide, 0.3 g Brij 35 (nonionic surfactant, ICI Chemical Corp.) and 0.15 g Brij 98 (polyethoxylated lauryl alcohol, ICI Chemical Corp.). This mixture is stirred at 60–65° C. for 2 hours to give a stable dispersion.

EXAMPLE 10

Synthesis of Ethylene-1,2-bis-(3-perfluoroalkyl-2-methylene piperidin-1-yl)

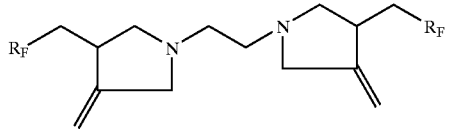

4.1 g (67.5 mmol) of ethylenediamine (from Aldrich) and 23.2 g of deionized water are placed into a round-bottomed flask equipped with a stirrer, nitrogen inlet, condenser and a thermometer. Then 23.4 g (299.3 mmol) of allyl chloride is added while mixture is stirred and heated to 45° C. After 20 minutes, a solution of sodium hydroxide (10.1 g, 252 mmol, 33%) is added and the reaction mixture is stirred for 3.5 hours at 45° C., after which time the N-allylation reaction is complete as determined gas chromatography and chloride ion titration (AgNO₃). The temperature is then lowered to 40° C. and additional sodium hydroxide (2.3 g, 5.75 mmol, 50%) is added along with 1.5 g (7.32 mmol, 88%) of sodium hydrosulfite. Then 79.3 g (133.1 mmol) of perfluoroalkyl iodide (Zonyl Tela-N) and 8.5 g of hexylene glycol are added and the reaction mixture is stirred at 45° C. for three hours to allow for free radical addition of the perfluoroalkyl iodide. Conversion of R$_F$-iodide is determined by gas chromatography to be greater than 99%. The reaction mixture is then heated to 70° C., sodium hydroxide (13.5 g, 337 mmol, 50%) is added and the reaction mixture is stirred for an additional 5 hours to allow for deiodination, which is complete at this time based on titration for chloride.

The reaction mixture is cooled and extracted into diethyl ether and isolated as a dry solid which is characterized by NMR.

EXAMPLE 11

Synthesis of 1,3-bis-(3-Perfluoroatkyl-2-methylene piperidin-1-yl)-2-hydroxy Propane

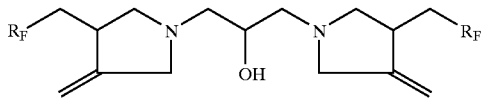

a) synthesis of N,N,N',N'-Tetraallyl-2-hydroxy-1,3-propane Diamine 17.4 g (173.8 mmol) of diallylamine (from Aldrich) and 10.0 g of deionized water are stirred in a round-bottomed flask at 55° C. while 8.08 g (86.48 mmol) epichlorohydrin is added from an addition funnel. After 30 minutes the addition is complete. Then sodium hydroxide (10.0 g, 125 mmol, 50%) is added to the reaction mixture and it is stirred for an additional 3.5 hours, after which time the alkylation is complete as determined gas chromatography. The temperature is then cooled to 25° C. and the pH is made alkaline with caustic. The product is extracted from the reaction mixture with ether (three times, 25 ml). On removal of the ether a clear yellow liquid is obtained with a purity of 98.6% (GC and NMR).

b) 5.0 g (19.97 mmol) of the above tetraallyldiamine, sodium hydroxide (1.5 g, 3.75 mmol, 20%) and 2.1 g of 2-propanol are placed into a round-bottomed flask equipped with a stirrer, nitrogen inlet, condenser and a thermometer. The mixture is heated to 50° C. Then 23.15 g (39.8 mmol) of perfluoroalkyl iodide (Zonyl TelA-N) is added along with 0.41 g (2.0 mmol, 88%) of sodium hydrosulfite as initiator. The reaction mixture is stirred at 55° C. for three hours, resulting in >99% conversion of R$_F$-iodide by GC analysis. The temperature is raised to 60° C. while 9.0 g of 50% NaOH is added. Then the mixture is stirred for 5 hours at 60° C., after which time the deiodination is complete as determined by iodide titration. The reaction mixture is washed free of halides by adjusting the pH to alkaline with caustic and extracting with methyl propyl ketone.

A cationic emulsion is made using Ethoquad 18/25 (polyethoxylated octadecylamine from Akzo-Nobel, 1.2 g), deionized water/acetic acid (140.0 g/2.9 g), and isopropyl acetate (35 g). After stirring at 65° C. for 15 minutes, the mixture is passed three times though a high pressure homogenizer. After the solvent is removed by vacuum at 50° C., a stable aqueous emulsion is obtained having 14% solids which is useful as a paper size.

EXAMPLE 12

Synthesis of bis-(3-Perfluoroalkyl-2-methylene piperidinyl)-succinamide

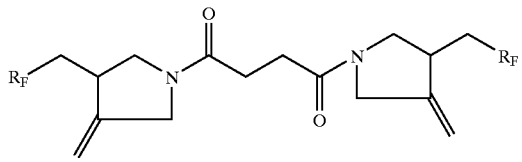

5.02 g (8.8 mmol) of the R$_F$-pyrrolidine of Example 5 is placed into a round-bottom flask equipped with a stirrer, nitrogen inlet, condenser and a thermometer. The mixture is stirred at 125° C. under a constant nitrogen flow while 0.66 g (4.44 mmol) of dimethyl succinate (from Aldrich) is added. The reaction mixture is stirred at 170° C. for one hour, after which time none of the starting materials remain as determined by gas chromatography. The bis-succinamide is obtained as a black resin which is soluble FREON-113. The structure is verified by NMR.

EXAMPLE 13

Synthesis of Poly-(perfluoroalkyl Pyrrolidine-acrylamides)

A flask fitted with a reflux condenser and a mechanical stirrer is charged with 9.0 g (14.5 mmoles) of the perfluoroalkyl pyrrolidine of Example 2, (1.65 g, 8.9 mmole) N,N-diethylaminoethyl methacrylate, 0.9 g (9.0 mmole) methyl methacrylate and 10.0 g methyl isobutyl ketone. The flask is purged with nitrogen at 40° C., and 0.12 g azobisisobutyronitrile (AIBN) is added. The polymerization is performed by stirring the mixture at 65 to 70° C for 4.5 hours. To the polymerization mixture are added another 0.03 g AIBN and 0.07 g methyl methacrylate. The mixture is then stirred at 65° C. for 16 hours, forming a very viscous gel-like mass. It is believed this is due to the formation of high molecular weight polymer resulting from crosslinking via the exocyclic double bond present in the monomer.

Example 14 is performed without methyl methacrylate as a third comonomer.

EXAMPLE 14

The procedure of Example 13 is repeated with the following charges of monomers and solvents: 6.0 g (9.7 mmoles) of the perfluoroalkyl pyrrolidine of Example 2, 1.6 g (8.6 mmoles) N,N-diethylaminoethyl methacrylate and 10.0 g methyl isobutyl ketone. The flask is purged with nitrogen at 40° C., and 0.07 g of azobisisobutyronitrile are added. The polymerization is carried out by stirring the mixture at 65 to 70° C. for 4.0 hours; then another 0.03 g of azobisisobutyronitrile are added and the mixture is stirred at 68° C. for another 5 hours, after which time the reaction is stopped due to excessive viscosity. The reaction mixture contains 5% of unreacted perfluoroalkyl pyrrolidine monomer. An aqueous solution of acetic acid (0.7 g acetic acid in 25 g water) is added and the mixture is stirred for 15 minutes. The mixture is then transferred to a round bottom flask and methyl isobutyl ketone is removed under vacuum, resulting in a yellow aqueous copolymer solution having a pH of 5 and 18% solids.

Examples 13 and 14 resulted in highly viscous mixtures and partial crosslinking during polymerization. The following polymerizations are performed using a chain transfer agent to control the molecular weight and hence the viscosity.

EXAMPLE 15

A flask fitted with a reflux condenser and a mechanical stirrer is charged with 10.0 g (16.0 mmoles) of the perfluoroalkyl pyrrolidine of Example 2, 2.6 g (14 mmoles) N,N-diethylaminoethyl methacrylate and 8.0 g methyl isobutyl ketone. The flask is purged with nitrogen at 40° C., then 0.13 g dodecane thiol and 0.1 g of 2,2'-azobis(2-methylbutanenitrile) (Vazo-67) are added. The polymerization is carried out by stirring the mixture at between 68 and 72° C. for 4.0 hours, after which time another 0.04 g of Vazo-67 are added and the mixture is stirred at 70° C. for another 6 hours. An aqueous solution of acetic acid (1.2 g acetic acid in 40 g water) is added and the mixture is stirred for 15 minutes. It is then transferred to a round bottom flask and methyl isobutyl ketone is removed under vacuum, resulting in a yellow aqueous copolymer solution having a pH of 5 and 18% solids.

In Examples 16 and 17, N,N-dimethylaminoethyl methacrylate is used as the amino monomer. In order to evaluate the effect of other comonomers, N-vinyl pyrrolidinone is also used as the third comonomer in Example 17.

EXAMPLE 16

A flask fitted with a reflux condenser, and a mechanical stirrer is charged with 15.0 g (24.0 mmoles) of the perfluoroalkyl pyrrolidine of Example 2, 3.4 g (21.6 mmoles) of N,N-dimethylaminoethyl methacrylate; and 12.0 g of methyl isobutyl ketone. The flask is purged with nitrogen at 40° C.; then 0.15 g of dodecane thiol and 0.15 g of Vazo-67 are added. The polymerization is performed by stirring the mixture at between 68 and 70° C. for 4.0 hours. To the polymerization mixture are added 0.3 g of dimethylacrylamide and another 0.04 g of Vazo-67. The mixture is then stirred at 68° C. for 6 hours. An aqueous solution of acetic acid (2.1 g acetic acid in 50 g water) is added, and the mixture is stirred for 15 minutes. It is then transferred to a round bottom flask and methyl isobutyl ketone is removed under vacuum, resulting in a yellow aqueous copolymer solution having a pH of 4 and 23% solids.

EXAMPLE 17

A flask fitted with a reflux condenser and a stirrer is charged with 12.0 g (19 mmoles) of the perfluoroalkyl pyrrolidine of Example 2, 1.5 g (9.5 mmoles) of N,N-dimethylaminoethyl methacrylate; 0.9 g (8.1 mmoles) of N-vinyl pyrrolidinone and 11.0 g of methyl isobutyl ketone. The flask is purged with nitrogen at 40° C. To the flask are added 0.1 g of dodecane thiol and 0.1 g of Vazo-67. The polymerization is performed by stirring the mixture at between 68 and 70° C. for 4.0 hours. To the polymerization mixture is added another 0.05 g of Vazo-67, and the mixture is stirred at between 65 to 70° C. for 5 hours. An aqueous solution of acetic acid (1.0 g acetic acid in 90 g water) is added, and the mixture is stirred for 15 minutes. It is then transferred to a round bottom flask and methyl isobutyl ketone is removed under vacuum, resulting in a yellow aqueous copolymer solution having a pH of 5 and 17% solids.

EXAMPLE 18

Synthesis of {3-[3-(Perfluoroalkyl)methyl-4-methylene-pyrrolidin-1-yl]-2-hydroxy-propyl}-trimethylammonium Chloride a) At 74° C., 33.1 g (0.154 mol, 70.6%) glycidyltrimethylammonium chloride are added over 30 minutes to 15.0 g (0.154 mol) diallylamine and 12 g deionized water while an exotherm is controlled at 75–80° C. by external cooling. After the addition, the clear yellow solution is stirred at about 78° for 90 minutes, after which time less than 1 mol % of diallylamine is unreacted according to GC analysis. Spectral analysis confirms the suggested product.

b) $R_F$-iodide Addition 26 g perfluoroalkyl iodide (43.7 mmol) ($R_F$-1, DuPont's Zonyl TelA-N) are added to a solution of 16.9 g (43.7 mmol) of the reaction product of Example 18a in 15.0 g water and 15.0 g 2-propanol, followed by 0.43 g (2.18 mmol, 88%) sodium dithionite. The reaction mixture temperature spontaneously increases from 22° C. to 48° C. After cooling and stirring for 90 minutes at 25–30° C., less than 1 wt. % $R_F$-1 is unreacted as determined by GC. Then 5.2 g (65.5 mmol) sodium hydroxide are added and the mixture is stirred at 65° C. for 4.5 hours to carry out the dehydroiodination step. The product mixture is then poured into 1 liter of ice water, filtered, and dried to give a tan solid in quantitative yield. Proton NMR confirms the suggested structure:

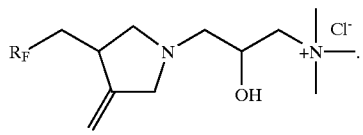

EXAMPLE 19

The following example shows the usefulness of the novel compounds of the present invention as external paper sizes.

External Size Application:

Neutralized test solutions are added to a 4% aqueous solution of paper makers starch (Stayco M, oxidized starch, from Staley Corp.) and then applied to unsized paper by padding (paper dipped through starch solution, and passed through single nip rollers). The resulting sheets are dried at ambient conditions for 15 minutes, then 3 minutes at 200° F. (86.6° C.) in an "Emerson Speed Drier" (heated metal plate with a canvas cover).

OIL AND GREASE RESISTANCE TESTS

Oil Kit Test:

The oil repellency of the surface is determined by using the TAPPI UM 557 OIL KIT TEST, which consists of determining with which of twelve castor oil-heptane-toluene mixtures, having decreasing surface tension penetration occurs within 15 seconds; ratings go from 1, lowest, to 12.

Ralston-Purina (RP2) Test:

Grease resistance is determined with the Ralston-Purina test for pet food materials; RP-2 Test, Ralston-Purina Company, Packaging Reference Manual Volume 06—Test Methods. In summary, cross-wise creased test papers are placed over a grid sheet imprinted with 100 squares. Five grams of sand are placed in the center of the crease. A mixture of synthetic oil and a dye for visualization is pipetted onto the sand and the samples are maintained at 60° C. for 24 hours. Ratings are determined by the percentage of stained grid segments, using at least two samples.

Turpentine Test: a preliminary test to determine rates at which oil or grease can be expected to penetrate the paper is conducted according to TAPPI T454om-94.

WATER AND ALCOHOL RESISTANCE TESTS

Cobb Size Test

Water resistance is determined using the Cobb Sizing test as described in TAPPI T 441om-90.

IPA Resistance Test

In this test drops of isopropanol—water mixtures are placed on paper and after 3 minutes the under side of the paper is monitored for penetration. if no penetration has occurred, a mixture with the next higher IPA content is applied. The rating is based on the highest % by weight of IPA which does not penetrate. Ratings are based on 5% IPA increments.

Pet food—"Felix" Test:

This is a very stringent test. French "Felix" brand cat food is placed as a 2 cm thick layer on 100 cm$^2$ of treated paper; this sample is then put under a weight of 7 kg and kept in an environmental chamber at 70° C. and 67% moisture for 16 hours. The paper is then visually inspected for signs of fat penetration, which is expressed in area %. Any value below 15% is considered passing. Cat food is used because it is a very aggressive substance, containing phosphoric acid (to prevent kidney stones).

Pet food "Eukanuba" test:

The same procedure is used as described above, but with Eukanuba brand pet food and under dry conditions.

The following table shows the performance of the inventive compounds in comparison with commercial products. Note that the performance of the inventive compounds in pet food tests is similar to that of commercial polymeric compounds, whereas comparable commercial low molecular weight compounds fail in pet food tests.

| Compound of Example No. | % F appl. | Oil and Grease | | | Resistance to Polar Solvents | | Pet Food Tests | |
|---|---|---|---|---|---|---|---|---|
| | | Oil Kit Test | RP-2 Test | Turp. Test, secs. | Cobb 2 min. % | IPA Test % | FELIX 70° C. % | EUKANUBA 70° C. % |
| 6 | 0.06 | 7 | 0,0 | 900 | 72 | 0 | | |
| | 0.07 | 7 | 0,0 | 1200 | 72 | 0 | | |
| | 0.09 | 10 | 0,0 | 1800 | 61 | 0 | 36 | 0.2 |
| 8 | 0.07 | 9 | 2 × 0 | 900 | 65 | 0 | | |
| | 0.09 | 11 | 2 × 0 | 1800+ | 45 | 0 | | |
| | 0.12 | 12 | 2 × 0 | 1800+ | 32 | 1 | 15 | 0 |
| 9 | 0.07 | 5 | 4 × 0 | 30 | 46 | 1 | | |
| | 0.09 | 6 | 4 × 0 | 60 | 23 | 10 | | |
| | 0.12 | 9 | 4 × 0 | 1800+ | 22 | 40 | 10 | 0 |
| 10 | 0.05 | 7,7 | 4 × 0 | 90 | 41 | 5,0 | 35 | |
| | 0.07 | 8,9 | 4 × 0 | 1800+ | 25 | 10,0 | 15 | |
| | 0.10 | 9,12 | 4 × 0 | 1800+ | 23 | 20,2 | 8 | 0 |
| 4 | 0.07 | 8 | 0; 0.1 | 720 | 33 | 10 | | |
| | 0.08 | 9 | 0.1 | 1500 | 30 | 10 | | |
| | 0.12 | 10 | 2 × 0; 1 | 1800+ | 21 | 20 | 9 | 0 |
| 15 | 0.13 | 9 | 0; 0 | >1800 | 22 | 50 | 5 | 0.05 |
| 17 | 0.11 | 10 | 0.1 | >1800 | 21 | 20 | 9 | 0 |
| FX-850* | 0.16 | 7 | 0, 0.1 | 1800+ | 61 | 100 | 26 | 7 |
| For325* | 0.12 | 12 | 0,0 | 1800+ | 34 | 100 | 22 | 0 |
| P-208** | 0.11 | 9 | 0, 0.2 | 1800+ | 68 | 0 | 80 | 0 |
| FC-807** | 0.10 | 12 | 2 × 0 | 1800+ | 83 | 0 | 100 | 100 |

* = polymers; ** = small molecules

EXAMPLE 20

Internal Size Application and Testing:

Six grams of dry recycled pulp consisting of 70% hardwood and 30% soft-wood is diluted in 289 ml distilled water and thoroughly dispersed in a blender. To this pulp slurry is added the required amount of a 1% solution of the test compound in distilled water and mixed in for 5 minutes. Then 6 ml of a 1% aqueous solution of cooked cationic starch is added and mixed in for an additional 5 minutes. To this mixture 24 ml of a 50% (on solids) dilution of a water-repellent adjuvant (alkylketene dimer, AKD, commercial product Hercon-76, from Nalco Chem. Corp.) are added and mixed in for another 10 minutes. The resulting slurry is diluted with an additional 500 ml of distilled water and mixed again. This mixture is then poured over a 100 mesh wire screen while a vacuum applied from below. This pulls the water from the pulp mixture to form a sheet on the screen. The wet sheet is removed from the screen and dried between another screen and a hard surface at a pressure of approximately 0.4 lb./in$^2$ at 110° C. for 1½ hours.

Hot-Oil Test:

One ml of hot (110° C.) corn oil is placed on the paper and the time is recorded for penetration to occur (20 minutes maximum). Paper made in the same manner, including the cationic starch and water-repellent adjuvant, but without a fluorochemical, demonstrates an oil kit number of <1 and holds the hot corn oil for less than one minute (begins to penetrate as soon as applied). The amount of oil absorbed is determined gravimetrically by weighing the paper before and after the hot-oil test, and after the surface oil has been removed.

The Oil-Kit Test is the same as that for the External Size.

Hot-Water Test:

One ml of a hot (83° C.) 5% lactic acid solution is placed on a paper plate; hold-out time and absorption are measured the same way as in the hot-oil test.

In this application water resistance is a function of the AKD (alkylketene dimer); it is important that the AKD cure is not inhibited by the fluorochemical additive. The test results show that the bis-pyrrolidine compound of Example 11 performs exceptionally well with the polymeric product being only slightly worse.

The following table shows the results:

| Exp. # | Compound Type | % F | OIL | WATER |
|---|---|---|---|---|
| 6 | R$_F$-pyrr. Succinamate | .07 | >20/0 | =20/32 |
| | | .15 | >20/0 | 1/51 |
| 9 | di-R$_F$-pyrr. Pyromellitate | .07 | 1/52 | >20/9 |
| | | .15 | 1/32 | =20/23 |
| 11 | bis-R$_F$-pyrrolidine | .07 | >20/0 | >20/7 |
| | | .15 | >20/0 | >20/7 |
| 4 | polyacrylamide | .07 | >20/0 | =20/18 |
| | | .15 | >20/0 | >20/46 |

What is claimed is:

1. A pyrrolidine of the formula III

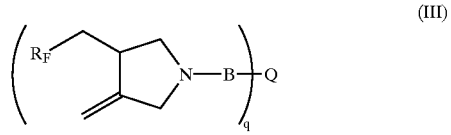

(III)

in which

R$_F$ is a monovalent perfluorinated alkyl or alkenyl, linear or branched organic radical having four to twenty fully fluorinated carbon atoms, B is a direct bond, —C(=O)— or —C(=O)—N—, q is an integer from 1 to 10 in which, when q is 1, Q is a monovalent organic radical with 2 to 200 carbon atoms and which can contain one or more unsaturated groups and is optionally interrupted by one or more —O— or —S— linkages or tert, amino groups, and which is unsubstituted or substituted by one or more hydroxyl, tert. amino, amide, $R_F$, —P(=O)(OH)$_2$, —SO$_3$H or —COOH groups, or is also NH$_2$ if B is —C(=O)—, and, when q is greater than 1, Q is a di- or polyvalent organic radical with 2 to 200 carbon atoms which can be interrupted by one or more —O— or —S— linkages, amide or tert. amino groups, and which is unsubstituted or substituted by one or more hydroxyl, tert. amino, amide or carboxyl groups; —C(=O)— or a di- or triradical derived from cyanuric chloride, with the proviso that if Q is —C(=O)—, B is a direct bond, and wherein any amino groups are optionally partially or fully salinized, quatemized or in the form of the corresponding N-oxides.

2. A compound according to claim 1, wherein $R_F$ is saturated and contains 4–12 carbon atoms, is fully fluorinated and contains at least one terminal perfluoromethyl group.

3. A compound according to claim 2, wherein $R_F$ is saturated and contains 6–10 fully fluorinated carbon atoms.

4. A compound according to claim 1, wherein q is 1 or 2.

5. A compound according to claim 1, wherein q is 1 and B-Q is —(CH$_2$)$_{1-3}$COOH; —CH$_2$—C(=O)NH$_2$; —C(=O)—CR=CH$_2$; —C(=O)COOH; —C(=O)—(CH$_2$)$_{2-3}$—COOH; —C(=O)—CH=CH—COOH; —C(=O)—C(=CH$_2$)—CH$_2$—COOH and —C(=O)—CH$_2$—C(=CH$_2$)—COOH; —C(=O)—(C$_6$H$_4$)—COOH; —C(=O)—(C$_6$H$_8$)—COOH; —C(=O)—(C$_6$H$_5$R$_F$)—COOH; —C(=O)—(C$_7$H$_6$)—COOH; —C(=O)—(C$_8$H$_8$)—COOH; —C(=O)(CH$_2$)$_8$CH=CH$_2$; —CH$_2$—CHOH—CH$_2$—O—CH$_2$—CH=CH$_2$; —C(=O)CH$_3$; —CH$_2$CH$_2$N(CH$_3$)$_2$; —C—CH$_2$CH$_2$CH$_2$N(CH$_3$)$_2$; —CH$_2$—CH(OH)—CH$_2$—N(CH$_3$)$_3$$^+$; —CH$_2$—CHOH—CH$_2$—O—(CH$_2$CHR—O)$_m$R$_1$; —P(=O)(OH)$_2$ or —SO$_3$H, in which R is hydrogen or methyl, m is a number from 1 to 20 and R$_1$ is hydrogen, an alkyl group with 1 to 20 carbon atoms, or a phenyl group substituted by p-octyl- or p-nonyl, or SO$_3$H.

6. A compound according to claim 5, wherein R and R$_1$ are hydrogen and m is a number from 1 to 10.

7. A compound according to claim 5, wherein B-Q is —C(=O)—CR=CH$_2$; —CH$_2$—COOH; —C(=O)—(CH$_2$)$_2$—COOH; —C(=O)—(C$_6$H$_4$)—COOH; —C(=O)—(C$_6$H$_5$R$_F$)—COOH or —C(=O)—(C$_6$H$_8$)—COOH.

8. A compound of the formula II

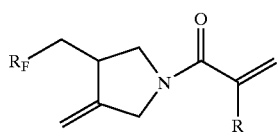

(II)

according to claim 5.

9. A compound according to claim 1, wherein q is 2, B is a direct bond and Q is —CH$_2$—CHOH—CH$_2$—O—(CH$_2$CHR—O)$_m$—((CH$_2$—CHR$_2$—O)$_n$—(CH$_2$—CHR$_3$O)$_l$)$_z$—CH$_2$—CHOH—CH$_2$; —CH$_2$CH$_2$—; or —CH$_2$—CHOH—CH$_2$—; wherein R, R$_2$ and R$_3$ are independently of each other hydrogen or methyl, m, n and l are a number from 1 to 20 and z is zero or 1; with the proviso that if R$_2$ is hydrogen, R and R$_3$ are methyl and vice versa; or —CH$_2$ CH$_2$—C(=O)—NH—CH$_2$—NH—C(=O)—CH$_2$CH$_2$—; or where B is —C(=O)—NH— and Q is the diradical hydrocarbon group of p- or m-toluene diisocyanate, isophorone diisocyanate, 3,3,4(3,4,4) trimethylhexane-1,6-diisocyanate or hexane-1,6-diisocyanate;

or where B is —C(=O)— and Q is —(C$_6$H$_2$)(—COOH)$_2$)—, —(C$_{13}$H$_6$O)(—COOH)$_2$)—, or is C$_2$-C$_{10}$alkylene or -alkenylene or —C$_6$-C$_{10}$arylene.

10. A compound according to claim 9, wherein B-Q is —CH$_2$—CHOH—CH$_2$—; —C(=O)—CH$_2$CH$_2$—C(=O)— or —C(=O)—(—C$_6$H$_2$(—COOH)$_2$)—C(=O)—.

11. A process to prepare a compound of the formula III

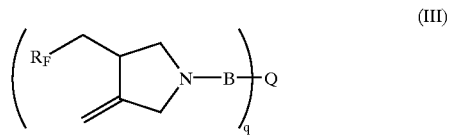

(III)

as defined in claim 1, which comprises reacting a 3-(perfluoroalkyl)methyl-4-methylenepyrrolidine of the formula I

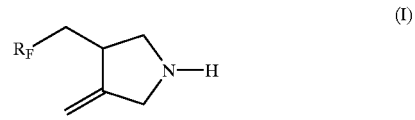

(I)

with an anhydride to form the corresponding amic-acid;

with a dianhydride to form the corresponding di-amic acid; with an acyl halide, a diacyl halide, an alkyl ester or a dialkyl ester, to form the corresponding amide or diamide;

with a halogenated organic compound to form the corresponding tertiary amine or tertiary amine-acid;

with a diisocyanate to form the corresponding di-urethane;

with an oxirane or a polyoxirane compound to form the corresponding hydroxy-tertiary amino compound;

or with a phosphoric acid group to form the corresponding phosphamic acid.

12. A process according to claim 11, wherein the anhydride is oxalic-, glutaric-, alkenyl-succinic-, succinic-, tetrahydrophthalic-, norbornene-, methendic-, maleic-, trimellitic or itaconic anhydride, the-dianhydride is pyromellitic anhydride or benzophenone-tetracarboxylic acid dianhydride, the acyl halide is benzoyl chloride or acetyl chloride, the diacyl halide is oxalylchloride, the alkyl or dialkyl ester is ethyl undecylenate or dimethyl succinate, the halogenated organic compound is 1,4-dichloromethylbenzene, chloroacetic acid, chloropropionic acid or chloroacetamide, the diisocyanate is isophorone diisocyanate, toluene diisocyanate, 1,6-diisocyanatohexane or 1,6-diisocyanato-3,3,4(3,4,4)-trimethylhexane, the oxirane or polyoxirane compound is epichlorohydrin, ethylene oxide, propylene oxide, cyclohexane oxide, styrene oxide, allyl glycidyl ether, the diglycidyl ether of bisphenol A, bisphenol F or 1,4-butanediol, and the phosphoric acid group is POCl$_3$, polyphosphoric acid or sodium metaphosphate.

13. A process to prepare a 1-acryloyl-3-(perfluoroalkyl) methyl-4-methylene compound of the formula IIa

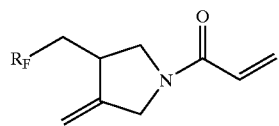

where $R_F$ is a monovalent perfluorinated alkyl or alkenyl, linear or branched organic radical having four to twenty fully fluorinated carbon atoms, which comprises a) reacting 3-chloropropionyl chloride with diallylamine to form N,N-diallyl-3-chloropropaneamide, b) reacting the product of step a) with an $R_F$-iodide, where $R_F$ is as defined above, in an aqueous medium comprising from 5 to 50% by weight of a water-soluble cosolvent, a free radical initiator and a water-soluble aldehyde or an adduct of an aldehyde with a free radical initiator and c) dehydrohalogenating the product of step b) with a base.

14. A process according to claim 13, wherein the free radical initiator is 0.01 to 10 mole % based on the $R_F$-iodide of an alkali metal dithionite and the water-soluble aldehyde is formaldehyde or glyoxal, or the aldehyde adduct is hydroxymethane sulfinic acid, sodium salt.

15. A method of improving the resistance of a paper product to oil and grease, which comprises applying to paper as an external coating or to pulp in a size press, an amount of a compound according to claim 1 which is sufficient to deposit from 0.005 to 0.5% of organically bound fluorine by weight based on the dry paper weight.

* * * * *

UNITED STATES PATENT AND TRADEMARK OFFICE
CERTIFICATE OF CORRECTION

PATENT NO.      : 6,436,235 B1                                         Page 1 of 1
DATED           : August 20, 2002
INVENTOR(S)     : Marlon Haniff et al.

It is certified that error appears in the above-identified patent and that said Letters Patent is hereby corrected as shown below:

Column 8,
Example 1, the structural formula should read:

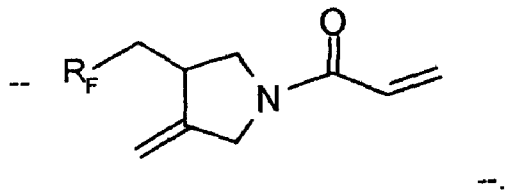
--.

Column 10,
Example 5, the structural formula should read:

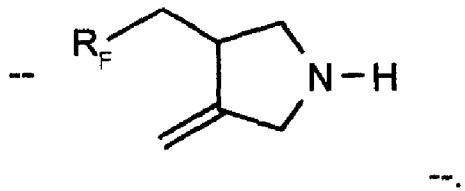
--.

Signed and Sealed this

Second Day of December, 2003

JAMES E. ROGAN
*Director of the United States Patent and Trademark Office*